United States Patent [19]

Kuratomi et al.

[11] Patent Number: 4,747,841
[45] Date of Patent: May 31, 1988

[54] METHODS AND INSTRUMENTS OF MOXIBUSTION

[76] Inventors: Yasuro Kuratomi, 8-2, 3-chome, Kita-Shinjuku, Shinjuku-ku, Tokyo; Keiko Miyauchi, 3-2-205-3, Takane-Dai Funabashi-shi, Chiba-ken, both of Japan

[21] Appl. No.: 919,549

[22] Filed: Oct. 15, 1986

Related U.S. Application Data

[63] Continuation of Ser. No. 713,489, Mar. 19, 1985, abandoned.

[51] Int. Cl.⁴ ................................................. A61F 7/00
[52] U.S. Cl. ..................................... 604/291; 604/24; 604/304; 128/399; 424/447
[58] Field of Search ................ 74/3 A, 3 B, 3 C, 3 D, 74/3 R; 604/24, 293, 304, 306, 360, 364, 372–374, 897, 19, 23, 289–291, 298, 307, 896; 128/156, 399, 400

[56] References Cited

U.S. PATENT DOCUMENTS

| | | | |
|---|---|---|---|
| 696,441 | 4/1902 | Holmes | 604/291 |
| 1,235,022 | 7/1917 | Fuji | 604/24 |
| 1,525,168 | 2/1925 | Davidson | 44/3 A |
| 1,609,958 | 12/1926 | Perrault | 44/3 A |
| 1,817,823 | 8/1931 | Ito | 604/24 |
| 1,831,669 | 11/1931 | Kono | 604/24 |
| 2,573,791 | 11/1951 | Howells | 604/291 |
| 3,946,733 | 3/1976 | Han | 604/291 |
| 4,106,478 | 8/1978 | Higashijima | 44/3 A |
| 4,114,591 | 9/1978 | Nakagawa | 44/3 R |
| 4,203,438 | 5/1980 | Shiu | 604/24 |
| 4,230,105 | 10/1980 | Harwood | 128/156 |
| 4,325,371 | 4/1982 | Atsumi | 604/291 |
| 4,366,804 | 1/1983 | Abe | 44/3 A |
| 4,685,911 | 8/1987 | Konno et al. | 604/291 |

FOREIGN PATENT DOCUMENTS

| | | | |
|---|---|---|---|
| 0084243 | 7/1978 | Japan | 604/306 |
| 0142074 | 11/1980 | Japan | 128/399 |
| 0156761 | 9/1982 | Japan | 128/399 |
| 0172974 | 10/1982 | Japan | 44/3 R |
| 0190441 | 11/1983 | Japan | 604/897 |
| 0015475 | 1/1984 | Japan | 44/3 R |
| 0147076 | 8/1984 | Japan | 44/3 R |
| 0145277 | 8/1984 | Japan | 44/3 R |

Primary Examiner—C. Fred Rosenbaum
Assistant Examiner—Mario Constantino
Attorney, Agent, or Firm—Oblon, Fisher, Spivak, McClelland & Maier

[57] ABSTRACT

A method of and apparatus for moxibustion comprising feeding air to a heat generating compositon in contact with a herb material comprising moxa, wherein said heat generating composition comprises a pyrogen and said herb material is located adjacent to a skin surface, wherein said feeding causes said pyrogen to generate heat by oxidation, whereby said herb material is heated and vaporized and the generated heat and vapor act on the skin, causing moxibustion effect.

7 Claims, 2 Drawing Sheets

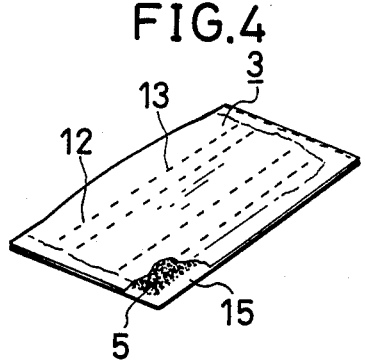
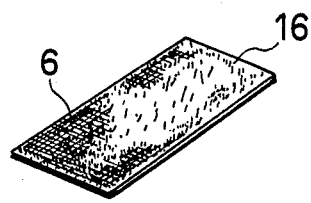
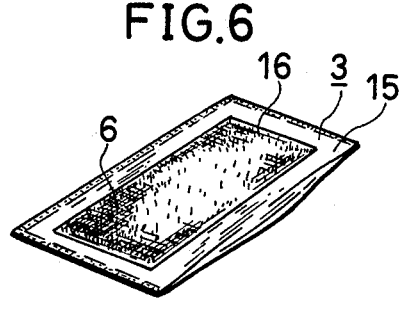
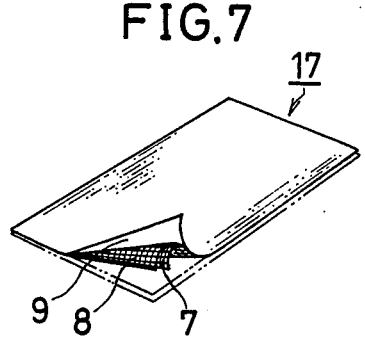
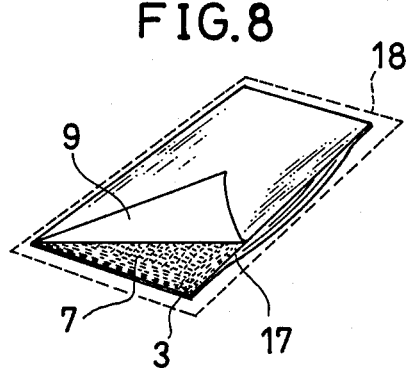

METHODS AND INSTRUMENTS OF MOXIBUSTION

This application is a continuation of application Ser. No. 713,489, filed Mar. 19, 1985, now abandoned.

BACKGROUND OF THE INVENTION

1. Field of the Invention

The instant invention relates to a method and apparatus of moxibustion.

Moxibustion treatment, applying moxa, long used in oriental medicine, manifests significant curative effects on the pain of the body's nervous system including the motor nerve, autonomic nerve, sensory nerve or on pains from psychoneurosis. The effects of moxibustion occur because moxa contains many ingredients including adenine, choline and highly volatile thymol. When the moxa is burnt the above ingredients become vapor and are easily absorbed through the skin to the tissues of the body or blood, and effectively act on the cells of the human body. Moxibustion has the specific feature of improving bodily functions by the stimulation of heat.

2. Description of the Background

In a conventional moxibustion treatment, moxa is placed on a certain key point on the surface of the patient's skin and the moxa is burnt by fire. This method has merit in that skin tissue is burnt and a part of the dead tissue is absorbed from the skin into the blood vessel, causing various immunizing materials to be made in the blood. On the other hand, this method has deficiencies in that it causes severe pain at and near the key spot, it leaves burn scars on the skin and generates a burnt smell and further must be performed by a specialist in moxibustion.

To avoid causing burn scars, no-scar moxibustion came to be used. This method involves applying ginger, garlic, onion, leek, miso, etc., on the skin, upon which moxa is placed and burnt. This method does not cause the subject to feel so hot, and leaves no scar. However, as this method utilizes warm heat, it does not utilize the ingredient of moxa fully.

SUMMARY OF THE INVENTION

Therefore, the instant invention aims to cure various diseases of the body using moxa and heat by causing the ingredient of moxa to be fully vaporized without using fire, while at the same time the moxibustion treatment of the instant invention fully exhibits the effects of heating without leaving any trace of a scar.

The instant invention feeds air to a pyrogen comprising a heat generating composition and causes the pyrogen to generate heat by oxidation. Herb material, comprising moxa or a mixture of moxa and other medical herbs, placed in contact with the pyrogen, is heated by the pyrogen and the ingredients of the medical herbs are vaporized. The resulting vapor and heat acts on the skin surface.

BRIEF DESCRIPTION OF THE DRAWINGS

The drawings indicate an example of the method of the moxibustion and the moxibustion apparatus of this invention.

FIG. 1 is a longitudinal sectional view of FIG. 1,

FIG. 4 is a perspective view of the third exemplary embodiment with a part of the package bag exposed, FIG. 5 is a perspective view of the herb supporting plate, FIG. 6 is a perspective view of the package body shown with herb supporting plate attached, FIG. 7 is a perspective view of the adhesion plate, and FIG. 8 is a perspective view indicating the whole assembly with an external part peeled away.

DESCRIPTION OF THE PREFERRED EMBODIMENTS

Figure 1:
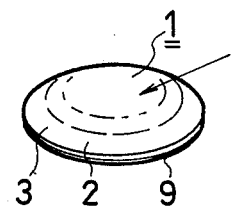
FIG. 1 is a perspective view of the first exemplary embodiment.

The pyrogen to be used in this invention comprises a heat generating composition consisting of iron powder, carbon, cellulose, chloride and water.

As the proper contents of the pyrogen, powdered iron is added in the amount of 42 wt. %–15 wt. % in the form of iron oxide; carbon is added in the amounts of 18 wt. %–22 wt. % as active carbon; cellulose is added in the amount of 15.5 wt. %–19 wt. % as excelsior; chloride is added in the amount of 3.7 wt. %–4.5 wt. % as sodium chloride and water is added in the amount of 11 wt. %–13.5 wt. %.

By making a mixture of the above heat generating components and feeding oxygen in the air to it, heat will be generated by oxidation of the iron oxide.

As the pyrogen used for this invention generates heat when contacted by oxygen in the air, it is necessary to store the pyrogen under conditions avoiding exposure to the air. For this purpose, an oxygen-impermeable package body is used to pack the pyrogen while not in use, said package body having the capacity to be made gas permeable when it will be used.

As for the means of packaging, a gas permeable internal package will be used. Namely, the pyrogen is accommodated in a package formed of woven fabric of synthetic resin, cotton, etc., said package thereby being gas permeable, or said package is prepared with a number of ventilation holes. The exterior of the internal package is covered with an external package formed of a non-permeable material such as a synthetic resin film or thin plate, preventing the pyrogen from contacting air; the external package is torn off at the time of application, thus feeding oxygen in the air to the pyrogen.

The package may also be made so that a non-permeable envelope (e.g., formed of a synthetic resin film, thin plate or unwoven fabric) will be perforated at the time of use. It can also be previously prepared with ventilation holes and sealed with a sealing plate, and the sealing plate will be peeled off at the time of application to open the ventilation holes.

The pyrogen as described above can be adjusted for the desired heat generation time and temperature by adjusting the composition of the material or the ventilating structure. However, normally 10 g–20 g of the pyrogen is required according to the type of pyrogen used. Contact of the pyrogen with oxygen results in the generation of heat for a period of 3 hrs–4 hrs for the small quantity (10 g) and 5 hrs–6 hrs for the large quantity (20 g). Temperatures of 65° C. are common at the heat generation source while the temperature at the point of contact with human skin is about 40° C.–45° C.

The herb material can be moxa or moxa mixed with ginger, garlic, Swertia japoneca, Angelica utilis or other materials, to increase the effect further. The quantity of 1 g to 3 g of herb material will be used.

The herb material can be placed in the package as is. However, it is more convenient to use a herb supporting broad made of flexible synthetic unwoven fabric, paper, cloth, etc., coated on one side with adhesive, such that the herb material is pressingly adhered to the adhesive. The herb material should be in a condition capable of contacting with pyrogen, because the herb material will be vaporized by heating of the pyrogen and so act on the skin. Therefore, herb material shall be packed in the package so that it may make contact with the bag containing pyrogen, or the above herb supporting board adhered with herb material will be placed so as to contact the pyrogen-containing bag.

Further, the skin side of the package body is structured to be opened, and this opening may be completely opened, packed so that gas permeability will be maintained, or pasted with a separate piece having gas permeability; the heat generating from the pyrogen and the vapor generating from the herb will act on the skin surface through this opened place, and the effect of moxibustion can be expected.

In addition, the skin-side face of the package body may be formed to allow it to be moved to arbitrary positions during use, or applied with adhesive so that it will be adhered to the skin surface corresponding to the key point.

The instant invention heats the herb material by the heat of oxidation of the pyrogen, and vaporizes the herb ingredients by this heat. Infrared heat is radiated by this vapor of the composition and the generated heat acts on the skin surface, and stimulates the function of the cells.

The instant invention heats the herb material by the heat generated by the oxidation of pyrogen, causing the herb material to vaporize. This vapor is supplied to the skin surface. This eliminates the danger of using fire as in the conventional method. Therefore, the use is simple, easy and safe as it does not leave a burn scar on the skin and does not generate a burning smell, but does stimulate cells by means of infrared heat.

The components included in 20 grams of the pyrogen are as follows:

| Iron oxide | 90 mesh | 46.4 wt. % |
| --- | --- | --- |
| Active carbon | 100 mesh | 20 wt. % |
| Excelsior | | 17.2 wt. % |
| Sodium chloride | | 4.1 wt. % |
| Water | | 12.3 wt. % |

The above pyrogen is placed in an internal package body made of unwoven fabric of synthetic resin. Many small ventilation holes are prepared in the internal package body. Paper adhered with 2 g of simple moxa is installed in the internal package body so that the paper containing moxa will contact the package body containing pyrogen. The moxa side of the paper is held by adhering gas-permeable weaving cloth to the internal package, and the whole is wrapped in a non-permeable external package body. When the external package is torn for application, the pyrogen generates heat for 5 hrs–6 hrs, and vapor generated from the moxa is applied to the skin surface.

EXAMPLES

Figure 2:
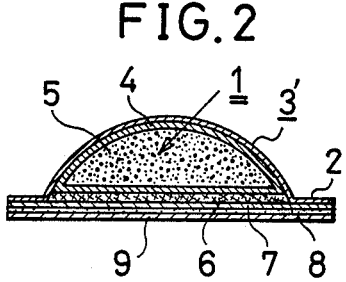

The first exemplary embodiment is constituted as shown in FIG. 1 and FIG. 2. Namely, the moxibustion apparatus 1 protrudes in circular form at the center part, and pyrogen 5 is included to the inside of a circular saucer type package body 3 made of non-permeable material such as paper, synthetic paper or synthetic resin, prepared with a flange shaped rim 2. Pyrogen 5 is a heat generating composition covered by a non-permeable bag body 4 made of non-permeable material such as synthetic resin film; to the under side of bag body 4 herb material 6, which is simple moxa or a mixture of moxa and other herbs, is filled in a stratum form to tightly contact with bag body 4. This herb material 6 may also be packed in paper or cloth having good gas-permeability and accommodated in the package body 3. Then, to the bottom side of the rim 2 supporting body 7 having good gas-permeability is adhered to support herb material 6, adhesive agent 8 is applied to the under surface of supporting body 7, and the adhesive agent 8 is pasted with non-gas-permeable peeling paper 9.

The first exemplary embodiment is constituted as described above. When using, first peel off the peeling paper 9 and paste to the skin surface corresponding to the key point of the human body by adhesive agent 8. Then perforate the outer side of the top wall of package body 3 and bag body 4 so as to open a ventilation hole to the pyrogen 5. Air intrudes through the said ventilation hole, and the pyrogen 5 will start to be oxidized by the oxygen in the air and will generate heat. This heat generation will cause herb material 6 to vaporize. The vapor of the herb ingredients, heat and infrared rays caused by the heating of the pyrogen will act on the surface of the skin through the supporting body 7, and the moxibustion effect can be expected.

Figure 3:
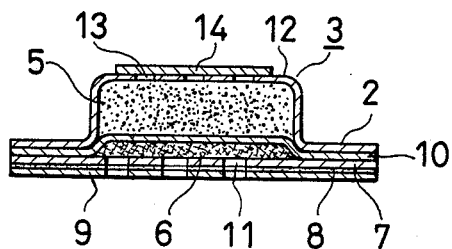
FIG. 3 is a sectional view of the second exemplary embodiment.

Now the second exemplary embodiment is described in accordance with FIG. 3; the center part protrudes in circular form and pyrogen 5 is accommodated in the inside of the package body 3 which is formed of a non-permeable material such as synthetic resin, etc., prepared with flange shaped rim 2. To the under side of the rim 2 a paper partition plate 10 is adhered to support pyrogen 5, the herb material 6 is placed in the center of the under side of the partition plate 10 so that the herb material will form a stratum, and supporting body 7 is adhered to the periphery of the under side of the partition plate 10 so as to support the herb material 6 to make is closely attach to the partition plate 10. This supporting body 7 is composed of a thin film of synthetic resin with many ventilating holes 11, the under side of the supporting body 7 is applied with adhesive agent 8, and peeling paper 9 is pasted to the adhesive agent 8. This peeling paper 9 may be prepared with air ventilating holes connected with the said ventilating holes 11.

In the top wall 12 of the package body 3 many air feeding holes 13 are prepared, and sealing plate 14 is pasted to the upper surface of the top wall 12, closing the air feeding holes 13 and preventing intrusion of air into the package body 3.

The second exemplary embodiment is constructed as above. When used, sealing plate 14 will be peeled off and the air feeding holes 13 are opened. The peeling paper 9 is peeled off and the apparatus is pasted to the skin corresponding to the key points of the human body with adhesive agent 8. Heat generated by oxidation of pyrogen 5 and vapor generated from herb material 6 are the same as the first exemplary embodiment, and the description of this step is omitted.

The second exemplary embodiment is very convenient in that air is fed to the pyrogen 5 by removing sealing plate 14.

Now the third exemplary embodiment is described in accordance with FIG. 4 through FIG. 8. Package body 3 is prepared in the following manner. The package body is constituted with a non-gas-permeable rectangular top wall 12 and bottom wall 15 formed of synthetic resin film. Then pyrogen 5 is filled between the top and bottom walls, and the circumference is heat-sealed to seal the pyrogen 5. In the top wall 12, air feeding holes 13 consisting of many small holes are prepared.

On the other hand, numeral 16 shown in FIG. 5 is the herb supporting plate comprising paper, unwoven fabric, gauze, etc., and formed in a rectangular shape, upon which herb material 6 comprising simple moxa or moxa mixed with other herbs is adhered by an adhesive agent or an electrostatic adhesion method. The herb supporting plate 16 formed in this way is adhered to or loaded onto the center of the bottom wall 15, so that the herb material 6 will be placed on the under side of package body 3, as shown in FIG. 6.

Further, adhesion plate 17 is formed by supporting plate 7 formed of gas-permeable cloth of unwoven fabric, etc., having characteristics of elasticity and wettability and being applied with adhesive agent 8 and pasted with peeling paper 9 as shown in FIG. 7. The supporting plate 7 is adhered to the circumferential rim of the bottom wall 15 of package body 3 so that it will cover the herb supporting plate 16. This is done by heating the circumferential rim of bottom wall 15 and adhering adhesive agent 8 to the circumferential rim.

The package body 3 constituted as above and adhered with adhesion plate 17 is packed within a non-gas-permeable external package bag 18 as shown by the dashed line in FIG. 8 to form the moxibustion apparatus.

The third exemplary embodiment is constituted as above, and for its application, external package bag 18 will first be torn off. By this way air is fed through the air feeding holes 13 of the package body 3, and the pyrogen 5 will generate heat by oxidation with oxygen in the air. Then, peeling paper 9 located to the one side of the package body 3 is peeled off, and the apparatus is applied to the skin corresponding to key points or affected parts of the human body with the adhesive agent attached to the supporting plate 7.

Warm heat generated by oxidation of pyrogen 5 is transmitted to herb material 6 through package body 3, and the herb material generates vapor which acts on the body from the supporting plate 7 through the skin and performs the moxibustion treatment.

Because the herb material 6 is in contact with the skin through supporting plate 7, which has the characteristics of elasticity and wettability, the supporting plate 7 comprises an air layer, which absorbs sweat and transfers heat to the body from the skin, acting as a thermal cushion, and successively releasing accumulated heat in the human body to outside of the body, and thus maintaining the temperature at the point of contact of the moxibustion apparatus with human skin at a level of 40° C.–45° C.

Further, in the above exemplary embodiment it was described to prepare air feeding holes 13 in the top wall 12 of the package body 3. However, the supporting plate 7 cannot be adhered for a complete seal with the skin surface. Therefore, air feeding holes 13 may be prepared in the bottom wall 15 so as to feed air through supporting plate 7 to heat pyrogen 5, or alternatively, both top wall 12 and bottom wall 15 may be prepared with air feeding holes.

Furthermore, when Culpak-processed kraft paper is used as the herb supporting plate 16 for adhering herb material 6, its black color causes it to be a good heat conductor, and the whole surface of the herb supporting plate 16 is heated even if only partial generation of heat by the pyrogen 5 occurred. Thus, good constituent vapor can still be generated.

What is claimed as new and desired to be secured by Letters Patent of the United States is:

1. A method of moxibustion, comprising the steps of:
   obtaining a means for supporting an herb material comprising moxa in contact with a heat generating composition, wherein said heat generating composition comprises a pyrogen comprising iron oxide, carbon, cellulose, sodium chloride and water;
   placing said means adjacent to a skin surface; and
   supplying air to said heat generating composition, wherein said supplying causes said pyrogen to generate heat by oxidation, whereby said herb material is heated and vaporized to release compounds comprising at least adenine, choline and thymol and the generated heat and vapor act on the surface of the skin.

2. The method of claim 1 wherein the herb material comprises moxa and one or more herbs selected from the group consisting of ginger, garlic, Swertia japoneca or Angelica utilis.

3. The method of claim 1, wherein said pyrogen comprises 42–51 wt. % iron oxide, 18–22 wt. % carbon, 15.5–19.0 wt. % cellulose, 3.7–4.5 wt. % sodium chloride and 11.0–13.5 wt. % water.

4. An apparatus for moxibustion comprising a package body having means for contacting a skin surface;
   means for supporting a herb material in contact with a first surface of said means for contacting a skin surface;
   a herb material comprising moxa contained in said means for supporting a herb material;
   means for supporting a pyrogen comprising iron oxide, carbon, cellulose, sodium chloride and water, in contact with a second surface of said means for supporting a herb material;
   said pyrogen contained in said means for supporting said pyrogen and means for introducing air into said pyrogen, such that air may enter the package body and oxidize the said pyrogen, causing the herb material comprising moxa to heat up and vaporize to release compounds comprising at least adenine, choline and thymol and act on the surface of the skin.

5. The apparatus of claim 4 wherein the herb material comprises moxa and one or more herbs selected from the group consisting of ginger, garlic, Swertia japoneca or Angelica utilis.

6. The apparatus of claim 4 wherein the means for supporting the herb material comprises black colored kraft paper adhered with herb material.

7. The apparatus of claim 4, wherein said pyrogen comprises 42–51 wt. % iron oxide, 18–22 wt. % active carbon, 15.5–19.0 wt. % cellulose, 3.7–4.5 wt. % sodium chloride and 11.0–13.5 wt. % water.

* * * * *